(12) United States Patent
Fitt et al.

(10) Patent No.: US 7,847,142 B2
(45) Date of Patent: Dec. 7, 2010

(54) HF ALKYLATION PROCESS WITH ACID REGENERATION

(75) Inventors: Jeffrey M. Fitt, Centreville, VA (US); Curtis A. Lawrence, Torrance, CA (US); Richard M. Janclaes, Long Beach, CA (US); Brett Keegan Johnson, New Orleans, LA (US); Michael W. Boyea, Potomac Falls, VA (US); Nicholas Steiner Conley, Redondo Beach, CA (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 598 days.

(21) Appl. No.: 11/878,828

(22) Filed: Jul. 27, 2007

(65) Prior Publication Data

US 2009/0029846 A1 Jan. 29, 2009

(51) Int. Cl.
*C07C 7/00* (2006.01)
(52) U.S. Cl. .................. 585/802; 585/724; 585/809; 585/310; 585/857; 585/723; 502/20; 502/36; 502/34; 502/35; 502/30; 422/188
(58) Field of Classification Search .................. None
See application file for complete search history.

(56) References Cited

U.S. PATENT DOCUMENTS 2,425,752 A * 8/1947 Hettick et al. ............... 585/704
3,956,416 A * 5/1976 Vora ............................ 585/718
3,993,706 A 11/1976 Mikulicz et al.
4,073,823 A 2/1978 Vora
4,239,931 A 12/1980 Mikulicz
4,473,442 A 9/1984 Funk et al.
5,264,647 A 11/1993 Eastman et al.
5,347,065 A 9/1994 Anderson
5,547,909 A 8/1996 Carlson
5,759,937 A 6/1998 Hovis et al.
6,413,897 B1 7/2002 Randolph et al.

* cited by examiner

*Primary Examiner*—Melvin C Mayes
*Assistant Examiner*—Smita Patel
(74) *Attorney, Agent, or Firm*—Glenn T. Barrett; Malcolm D. Keen

(57) ABSTRACT

The regeneration of HF alkylation acid in an alkylation unit is improved by withdrawing a vapor stream from the HF regenerator tower and condensing the stream to form a liquid fraction which is accumulated in a side distillation zone; the collected liquid fraction, comprising HF acid, water and some stripping medium is distilled in a batch or continuous type operation to drive off the HF acid (along with stripping medium) and the vapor is returned to the regenerator-stripper vessel. The distillation of the sidedraw liquid is continued until the composition of the liquid attains the azeotropic value or as near to that value as desired. The azeotrope, comprising water and acid can then be dropped out of the distillation vessel for disposal by neutralization in the conventional way.

10 Claims, 1 Drawing Sheet

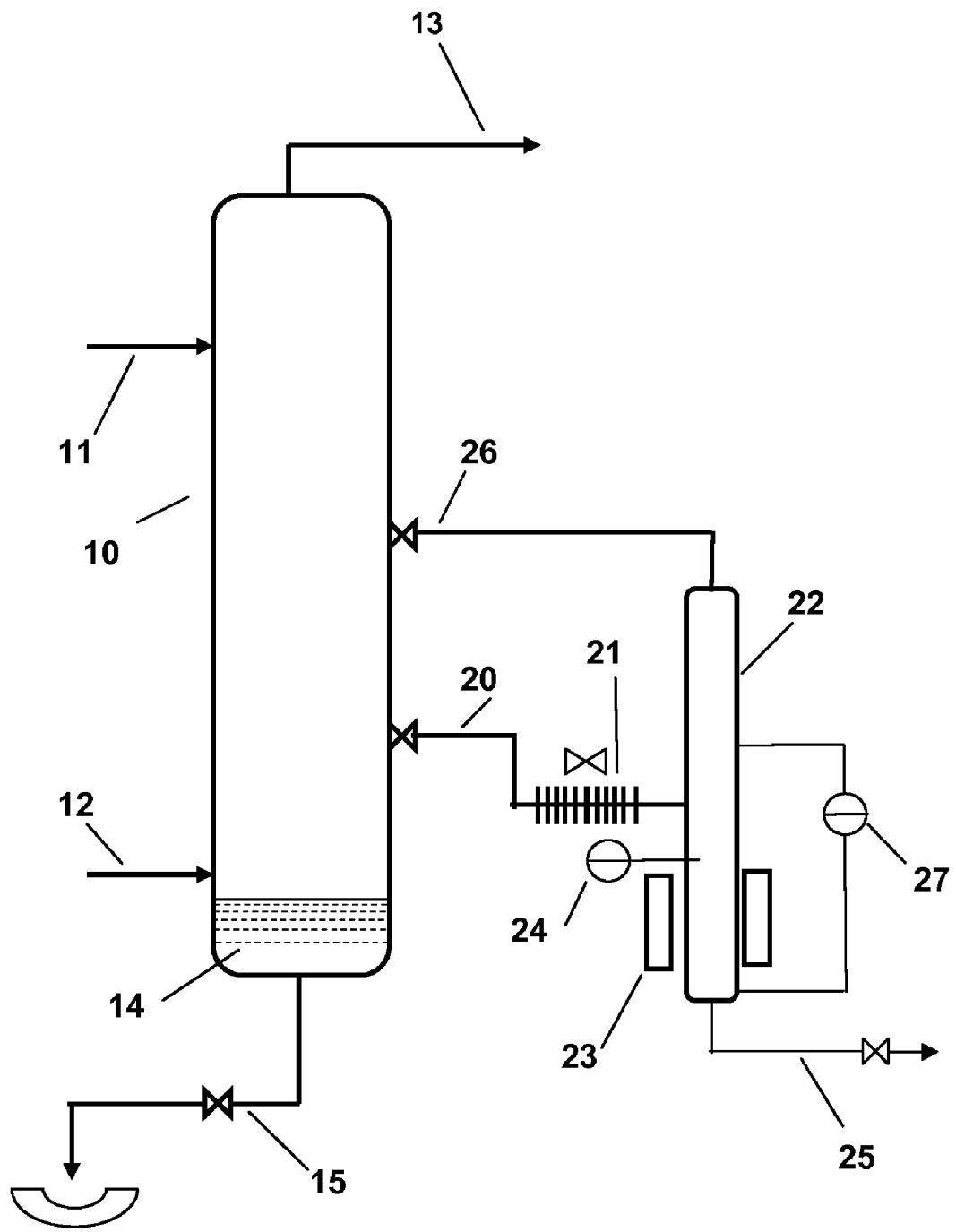

HF ALKYLATION PROCESS WITH ACID REGENERATION

FIELD OF THE INVENTION

This invention relates to iso-paraffin/olefin alkylation and more particularly, to hydrofluoric acid (HF) alkylation. In this specification, the term "alkylation" will be used to refer to the iso-paraffin/olefin alkylation process used to make gasoline blend components useful in aviation and motor gasolines and "HF alkylation" to this process using hydrofluoric acid as the catalyst.

BACKGROUND OF THE INVENTION

The iso-paraffin/olefin alkylation process is widely used to manufacture a high octane quality blend component for aviation and motor gasoline which is also valued for its relatively low vapor pressure, low sensitivity and, because of its freedom from aromatic components, its environmental acceptability. The process typically reacts a $C_3$ to $C_5$ olefin with isobutane in the presence of an acidic catalyst to produce the alkylate product.

Hydrofluoric and sulfuric acid alkylation processes have achieved widespread utilization to produce the highly desirable clean burning gasoline component. Although hydrogen fluoride, or hydrofluoric acid (HF) is toxic and corrosive, extensive experience in its use in the refinery have shown that it can be handled safely, provided the hazards are recognized and precautions taken. The HF alkylation process is described in general terms in *Modern Petroleum Technology*, Hobson et al (Ed), Applied Science Publishers Ltd. 1973, ISBN 085334 487 6. A survey of HF alkylation may be found in *Handbook of Petroleum Refining Processes*, Meyers, R. A. (Ed.), McGraw-Hill Professional Publishing, 2nd edition (Aug. 1, 1996), ISBN: 0070417962.

In order to improve the safety factors of the HF alkylation process, one option is to operate with a vapor suppressant additive in the alkylation acid. The vapor suppressant additives normally contemplated are those which reduce the volatility of the HF acid. Compounds of this type which have been proposed include organic sulfones, ammonia, amines such as the lower alkylamines (methyl to pentyl), pyridine, alkylpyridines, picoline, melamine, hexmethylenetetramine. A number of different sulfones have been proposed for this purpose but the one generally preferred is sulfolane (tetramethylenesulfone) with 3-methylsulfolane and 2,4-dimethylsulfolane also being suitable. A more detailed description of vapor suppressant additives of this type is given in U.S. Pat. No. 6,114,593 to which reference is made for this description. When a vapor suppressant additive is used the process is often referred to as modified HF alkylation (MHF).

In order to improve the operation of the HF alkylation process—whether with or without the vapor suppressant additive—as well as the economics of the process it is desirable to regenerate the HF alkylation acid by removing the water which accumulates as well as the polymeric by-product formed during the alkylation reactions; this polymer, comprising polymers of differing degrees of conjugation, is frequently referred to as "acid soluble oil" (ASO) since it is miscible with the HF acid phase. Removal of the ASO is necessary to preserve the concentration of the acid at the high level desirable for good alkylation performance while removal of water is required in order to reduce corrosion within the unit as well as to maintain product octane quality; normally, the acid concentration is maintained at 80 to 96 weight percent by the continuous or periodic addition of fresh acid and the regeneration of unit acid; the water content is normally kept in the range of 0.5 to 4.0 percent.

Regeneration of the HF alkylation acid may be accomplished either by internal or external regeneration. In the internal regeneration, a portion of the alkylation acid is injected into the isostripper and stripped off by heated isobutane. A regeneration process of this type is described, for example, in U.S. Pat. No. 4,239,931 (Mikulicz). A separate regeneration tower is used in external regeneration: a portion of the acid stream is stripped with light hydrocarbon in the regeneration tower, typically using a stream of hot isobutane which is subsequently returned to the unit reactor section (reaction settler) or the fractionation section (isostripper overhead) or is condensed and pumped back to the acid inventory in the reactor. Water removal is accomplished by suppressing operations in the external regenerator and dropping an acid/water phase out of the bottom of the column. The use of this stripping technique presents a number of problems: first, if the amount of stripping medium passed into the acid stream is sufficient to vaporize all or almost all of the HF acid, the volume of hydrocarbon is quite large, imposing a relatively large volume requirement on the stripping vessels. In addition, the heavy polymeric material tends to be entrained with the stripping medium and when this polymer enters the downstream equipment, it creates fouling problems, depositing on piping, condensers and the like. Conversely, if attempts are made to limit the volume of stripping medium relative to the acid stream, the stripping will be incomplete and acid will be lost when the bottoms material is dropped out of the regenerator tower. Second, it is difficult to control the regenerator liquid bottoms temperature. For additivated HF units (MHF units) using sulfolane additive, the problems encountered in the removal of the water are compounded by the fact that the distillation properties of sulfolane are similar to the heavy polymer so that the additive will be removed from the unit with the bottoms and so lost from the unit together with excessive amounts of acid.

An external regeneration method is described in U.S. Pat. No. 5,547,909 (Carlson). In the method described here, the acid phase from the settler is removed and a portion is routed to a separator column. Acid, free of ASO and water is removed as overhead and is recirculated to the settler. While this technique may be capable of improving on the conventional external separation by attempting to get closer to an azeotropic mixture of water, acid and polymer in the bottom of the tower, (acid content of the bottoms stream about 40-50%), it still fails to achieve a satisfactory level of acid recovery and significant losses of acid can be expected.

A regeneration process which is stated to remove polymer and water from the an MHF system is described in U.S. Pat. No. 5,759,937 (Hovis et al). In this process, the alkylation catalyst is subjected to stripping in a regenerator which has a vapor sidedraw of water, HF and stripper medium. This sidedraw is partially condensed resulting in a vapor stream comprising isoparaffin stripping medium and one or more liquid streams which may variously contain water and isoparaffin. In actual operation, however, the partial condensation stated to be critical is impractical since the control required for targeting the desired temperature is not easily accomplished by cooling. Operation in the practical realm, therefore, tends to condense the entire stream and to purge the condensed acid to the waste treatment plant. The composition of the purged stream is normally about 8 parts of acid to one part of water (90% acid), indicating that a substantial loss of acid takes place.

Accordingly, there is a need for an improved technique for regenerating HF alkylation acid by separating it from water and polymer as well as from vapor suppressant additives in MHF units.

SUMMARY OF THE INVENTION

We have now devised an improved HF acid regeneration apparatus as well as a technique for using it which can be used in conjunction with existing regeneration equipment. According to the present invention, the HF alkylation acid regeneration process takes a wholly vaporous sidedraw from the external stripper-regenerator tower and condenses it to form a liquid fraction which is accumulated in a side vessel. This collected liquid fraction comprising HF acid, water and some stripping medium is then heated to drive off the HF acid (along with stripping medium) and the vapor is returned to the regenerator tower. This distillation operation can be carried out either in batchwise or continuous mode. In batch mode, the stripper operation will normally be suspended pending completion of the water removal operation. The distillation of the sidedraw liquid is taken to the point that the composition of the liquid attains the azeotropic value or as near to that value as desired. The azeotrope, comprising water and acid can then be dropped out of the side vessel for disposal by neutralization in the conventional way. The advantage of this technique is that the amount of acid lost can, in favorable operation, correspond to little more than the quantity in the azeotrope, approximately one part with 1.5 parts of water (40% acid) with a consequent savings in acid make-up costs.

DRAWINGS

The single FIGURE of the accompanying drawings is a simplified schematic of the acid recovery device to remove the HF-water azeotrope from the alkylation unit.

DETAILED DESCRIPTION

The HF alkylation process of the present invention is carried out in the conventional manner as far as the alkylation reaction and separation of the hydrocarbon acid phases are concerned. In brief, a light $C_3$-$C_5$ isoparaffin, preferably isobutane, is alkylated with a light $C_3$-$C_5$ olefin in the presence of HF acid as an alkylation catalyst to produce, as the desired product, a hydrocarbon alkylate in the gasoline boiling range. As noted above, the parameters of the HF alkylation process are now well known and although the configurations of individual units may vary, their construction and operation are sufficiently well known to require no further description. Generally, a cooled reactor is used for the alkylation reaction itself with the olefin reactant being sparged into a stream of the HF acid catalyst and an excess of the isoparaffin reactant. From the reactor, the mixed phase stream is taken to an acid settler in which the denser acid is allowed to settle out by gravity from the less dense hydrocarbon phase comprising the alkylate product and unreacted isoparaffin. The alkylate product is recovered from the hydrocarbon phase by removal of the excess isoparaffin in the isostripper tower followed by a depropanizer and a product neutralizer. The polymer by-product, the acid soluble oil (ASO), accumulates in the acid phase which, along with minor amounts of water, is recirculated to the reactor. HF acid may be separated from polymer in the isostripper tower by introducing a minor amount of the acid phase as a slipstream with the large amount of alkylate and butanes feeding the tower. The acid flashes overhead and polymer and alkylate are taken out from the bottom of the tower. The limit on the amount of the acid in the hydrocarbon feed to the isostripper is set mainly by corrosion considerations: excess acid in the isostripper feed may lead to major corrosion problems in the isostripper overhead.

In the FIGURE, the acid regenerator tower 10 receives a minor portion of the circulating acid stream of HF alkylation acid as a slipstream from the acid region of the acid settler (not shown) which is introduced with the feed for the regenerator tower through line 11. This stream comprises HF acid, water and polymer (ASO) produced in the alkylation reactions along with minor amounts of hydrocarbon (isoparaffin and alkylate product). Stripping vapor comprising a hot stream of isoparaffin is introduced in the conventional manner at the foot of tower 10 through line 12. The fraction removed through overhead line 13 comprises isoparaffin in a relatively large quantity, water and HF acid; this fraction is returned to the alkylation reactor in the normal way. The polymer formed in the reaction is a higher boiling material and collects in a pool of liquid 14 at the bottom of the tower from which it can be drained periodically and taken to the site neutralization facility by way of line 15.

A vapor sidedraw is taken off regenerator tower 10 through line 20 which enters the tower in the vapor zone of the bottom tray section of the regenerator tower or from the vapor zone above the level of the liquid pool. Line 20 is fitted with cooling fins 21 which assist the cooling and condensation of the withdrawn vapor. An air fin design or forced fan cooling may be used as desired. Line 20 enters near the top of a small vertically-disposed distillation vessel 22 sized appropriately for the amount of water which is to be removed in each batch. This may be calculated by reference to the rate of water generation for the unit and the value to which it is desired, given considerations of product quality and unit corrosion, to maintain the water level in the circulating acid inventory. Because this vessel contains a rather corrosive mixture of HF acid and water, it should be made of corrosion resistant alloy such as Alloy 400 or Monel™ metal; because the size of the vessel is relatively small compared to other parts of the unit, its cost is acceptable. A heat source 23 such as a steam or electrical jacket or tracing heater is provided around the bottom of the vessel and a temperature sensor 24 about one third the way up the vessel. The heat source may be externally or internally applied but must be capable of providing fine control of the collected liquid temperature. A lower liquid outlet 25 enables the accumulated liquid to be periodically withdrawn from the vessel, as described below. A vapor return line 26 at the top of the vessel leads back into the regenerator tower at a higher level. Liquid level sensor system 27 is provided for monitoring minimum and maximum liquid levels within the vessel.

In a batch type mode, the device may be operated by first allowing the vapors from the regenerator tower to enter the vessel through line 20 by way of the valve at the tower port. Operation of the regenerator may be suspended during the regeneration steps. The vapors are cooled in line 20 to condense them partially or completely and fill vessel 22 to slightly below the level of the inlet line with condensed liquid; any uncondensed vapors escape through vapor return line 26 to the regenerator tower. Once full, the level is recorded and the valve on vapor line 20 at the tower port is closed. Heat is then applied to the liquid in the vessel to begin removing acid from the mixture in the vessel with the vapor passing back to the tower through vapor return line 26. The acid will be slowly vaporized from the collected liquid, reducing its volume to the point where only the acid/water azeotrope remains. The target temperature to which the distillation is carried out is determined by the operating pressure of the regenerator tower which also prevails in the side vessel by way of the vapor connection through line 26; lower tower pressures favor a greater concentration of water in the azeotropic mixture in the side vessel which is desirable from the economic point of view. Once the azeotropic concentration is achieved, the reduced solution may be drained from vessel 22 through line 25 and the heat removed from the lower part of the vessel. The removed liquid may then be taken to the site neutralization facility. The batch operation may be repeated as often and as frequently as necessary, as indicated empirically, to remove water from the unit's acid phase and so to maintain acid purity at the desired value.

The use of the vapor sidedraw connection located in the vapor zone of the regenerator tower above the liquid pool at the bottom of the tower precludes heavy polymer from entering the side vessel and so, even though the collected liquid is distilled, the problems associated with fouling are avoided. Light polymer components, typically formed from sulfur feed contaminants, may, however, be allowed to enter the side vessel by adjusting the draw level of line 20 in the tower or by adjusting tower operating conditions to allow light polymer vapor to enter the side vessel. The heavy polymer components can be periodically drained off from the regenerator tower in the accumulated liquid pool at the foot of the tower. The condensation of the vapor may be partial or complete, depending on the operation of the regenerator tower: partial condensation is preferred since this reduces the heating costs for the distillation step.

Continuous operation may be enhanced by packing the side vessel with appropriately sized packing or providing tray type internals and adjusting the vessel operating conditions to maintain target liquid temperature for a given system pressure. In this case, controls for liquid level, heat input and inlet stream cooling are required with the appropriate degree of accuracy. In this case, as with the batchwise mode, the essence is to carry out the reduction of the withdrawn, condensed liquid by the application of heat until the desired degree of concentration is required with removal of the vaporized acid and it return to the regenerator tower to be recirculated into the acid inventory.

The acid regeneration process is useful with conventional HF units as well as with those operated with a vapor suppressant additive, as described above.

The invention claimed is:

1. A process of regenerating HF alkylation acid from a mixture comprising HF acid, water and polymer formed during an HF olefin/isoparaffin alkylation process, which comprises:
    stripping the mixture comprising HF acid, water, the polymer and hydrocarbons in a regeneration zone by means of a stripping fluid to form a vapor from the mixture,
    withdrawing vapor from the regeneration zone and completely condensing the withdrawn vapor to form from the vapor a condensed liquid component comprising HF acid and water,
    heating the condensed liquid component to vaporize HF acid and returning the vaporized HF acid directly to the regeneration zone to increase the concentration of the water in the remaining condensed liquid component to a value closer to the azeotropic water/HF acid value and
    withdrawing the condensed liquid component having the increased concentration of water.

2. A process according to claim 1 in which the condensed liquid component is heated until an azeotropic mixture of water and HF acid is substantially attained.

3. A process according to claim 1 in which the stripping fluid comprises a $C_3$-$C_5$ isoparaffin.

4. A process according to claim 3 in which the isoparaffin is isobutane.

5. A process according to claim 1 in which the regeneration of the HF acid is carried out in a regeneration tower having a sidedraw in the vapor region through which the vapor from the regeneration zone is withdrawn into a vessel in which the heating of the condensed liquid component is carried out.

6. A process of regenerating HF alkylation acid from a mixture comprising HF acid and water formed during an HF olefin/isoparaffin alkylation process in which a light $C_3$-$C_5$ isoparaffin is alkylated with a light $C_3$-$C_5$ olefin to form a hydrocarbon alkylate product in the gasoline boiling range, which comprises:
    alkylating the light paraffin with the light olefin in the presence of HF alkylation acid as an alkylation catalyst to form an effluent comprising a hydrocarbon phase of hydrocarbon alkylate product and a separate phase of HF acid and water,
    separating the hydrocarbon phase from the HF acid phase,
    regenerating HF acid from a stream of the HF acid phase by stripping the stream in a regeneration zone by means of light isoparaffin as a stripping fluid, to vaporize HF acid and water from the stream,
    withdrawing a vaporous portion of the fluid from the regeneration zone comprising vaporized HF acid and water and completely condensing the withdrawn vaporous portion to form a condensed liquid component comprising HF acid and water in a distillation zone,
    heating the condensed liquid component in the distillation zone to vaporize HF acid and directly returning the vaporized HF acid to the regeneration zone, to increase the concentration of the water in the remaining condensed liquid component to a value closer to the azeotropic water/HF acid value and
    withdrawing the condensed liquid component having the increased concentration of water from the distillation zone.

7. A process according to claim 6 in which the isoparaffin comprises isobutane.

8. A process according to claim 6 in which the condensed liquid component is heated until an azeotropic mixture of water and HF acid is substantially attained.

9. A process according to claim 6 in which the condensed liquid component is withdrawn periodically from the distillation zone.

10. A process according to claim 6 in which the regeneration of the HF acid in the regeneration zone by stripping the stream in the regeneration zone forms a phase comprising an acid soluble oil polymer product of the alkylation which is withdrawn from the regeneration zone.

* * * * *